United States Patent
Izumi et al.

(10) Patent No.: US 6,225,729 B1
(45) Date of Patent: May 1, 2001

(54) ULTRASONIC PROBE AND ULTRASONIC DIAGNOSTIC APPARATUS USING THE PROBE

(75) Inventors: Mikio Izumi, Soka; Takashi Ikeda, Nagareyama, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/201,914

(22) Filed: Nov. 30, 1998

(30) Foreign Application Priority Data

Dec. 1, 1997 (JP) .................................................. 9-329827

(51) Int. Cl.⁷ .................................................. H01L 41/08
(52) U.S. Cl. .................................................. 310/334
(58) Field of Search .................................. 310/334–337, 310/326, 327

(56) References Cited

U.S. PATENT DOCUMENTS

| | | | |
|---|---|---|---|
| 3,362,501 | * 1/1968 | Lenahan | 310/334 X |
| 4,211,948 | * 7/1980 | Smith et al. | 310/334 X |
| 4,211,949 | * 7/1980 | Brisken et al. | 310/334 X |
| 4,348,904 | * 9/1982 | Bautista, Jr. | 310/334 |
| 4,430,593 | * 2/1984 | Gohlert et al. | 310/334 X |
| 4,507,582 | * 3/1985 | Glenn | 310/334 X |
| 4,523,122 | * 6/1985 | Tone et al. | 310/334 |
| 4,672,591 | * 6/1987 | Breimesser et al. | 310/334 X |
| 4,686,409 | * 8/1987 | Kaarmann et al. | 310/334 X |
| 5,327,895 | * 7/1994 | Hashimoto et al. | 310/334 X |
| 5,375,099 | * 12/1994 | Gill | 310/334 X |
| 5,511,296 | * 4/1996 | Dias et al. | 310/334 X |

\* cited by examiner

*Primary Examiner*—Mark O. Budd
(74) *Attorney, Agent, or Firm*—Antonelli, Terry, Stout & Kraus, LLP (57) ABSTRACT

An ultrasonic probe including a plurality of transducer elements for transmitting an ultrasonic wave and receiving a reflected ultrasonic wave from inside of an object to be examined, electrodes for applying a voltage to the transducer elements, and an acoustic matching layer for taking a matching of an acoustic impedance between the transducer elements and the object to be examined, wherein the acoustic matching layer includes a plurality of materials each of which has a different acoustic impedance and has an anisotropy in acoustic characteristic between an ultrasonic wave-transmitting direction from the transducer elements and a direction perpendicular to the ultrasonic wave-transmitting direction.

16 Claims, 7 Drawing Sheets

ULTRASONIC PROBE AND ULTRASONIC DIAGNOSTIC APPARATUS USING THE PROBE

CROSS-REFERENCE TO RELATED APPLICATION

The present application relates to the contents disclosed in the application Ser. No. 09/154694 filed Sep. 17, 1998 entitled "An ultrasonic probe having an acoustic matching layer in which the acoustic impedance is varied continuously in the thickness direction, a method of manufacturing thereof, and an ultrasonic diagnostic apparatus using the ultrasonic probe", by Shuzo Sano and Mikio Izumi and by the same Applicant as that of the present application.

BACKGROUND OF THE INVENTION

The present invention relates to an ultrasonic probe in which a plurality of transducer elements are arranged with a predetermined pitch so as to form each of channels which transmits an ultrasonic wave to an object to be examined and receives a reflected wave of the transmitted ultrasonic wave. More particularly, the present invention relates to an ultrasonic probe which can enhance a frequency characteristic and reduce a crosstalk between the respective channels, and an ultrasonic diagnostic apparatus using the ultrasonic probe.

Figure 11:
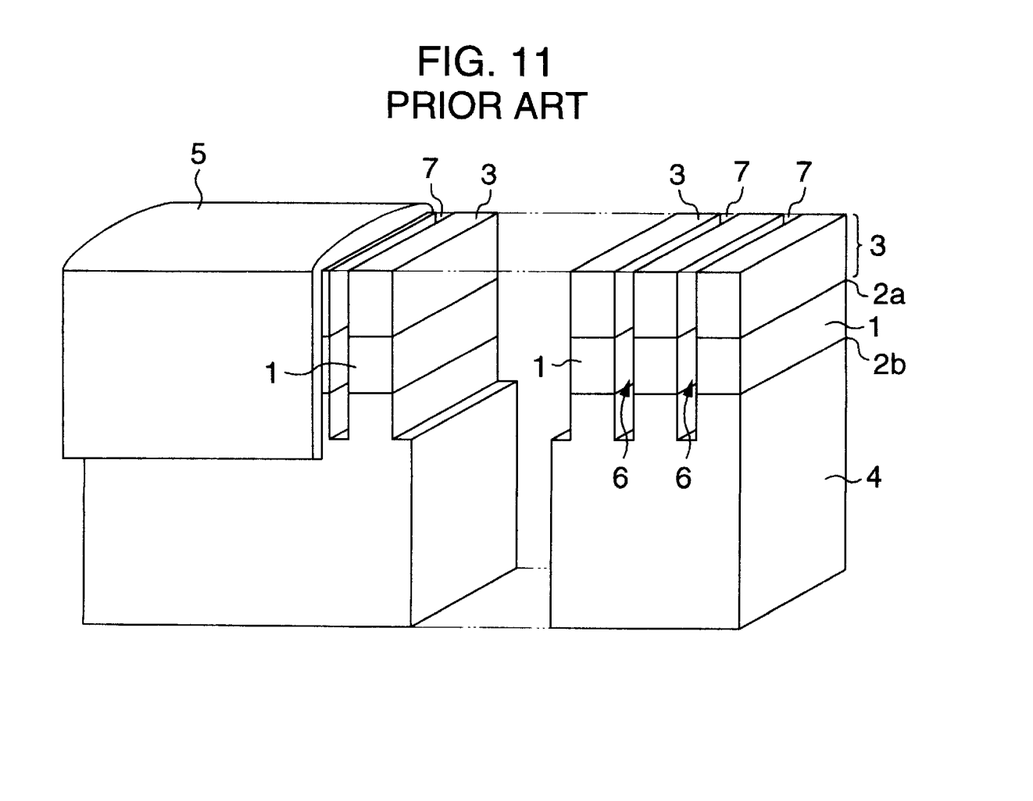
FIG. 11 is a partial cross sectional perspective view for illustrating a conventional ultrasonic probe.

A conventional ultrasonic probe, as shown in FIG. 11, includes a plurality of transducer elements 1, 1, ... which are arranged with a predetermined pitch so as to form each of channels for transmitting an ultrasonic wave and receiving a reflected wave from inside of an object to be examined, electrodes 2a, 2b provided on a front surface and a rear surface of each of the transducer elements 1, 1, ... so as to apply a voltage thereto, and an acoustic matching layer 3 for taking a matching of an acoustic impedance between the transducer elements 1, 1, ... and the object to be examined. In FIG. 11, a reference numeral 4 denotes a backing material for preventing an ultrasonic wave transmitted from the rear surface of the transducer element 1 from getting back again to the rear surface thereof. A reference numeral 5 denotes an acoustic lens provided over the above-described acoustic matching layer 3 so as to focus an ultrasonic beam transmitted from the front surface of the transducer element 1.

Here, concerning the acoustic matching layer 3, an acoustic impedance thereof is set to be an intermediate value between an acoustic impedance of the transducer element 1 and that of the object to be examined. Moreover, the acoustic matching layer 3 is formed so that a thickness thereof becomes equal to ¼th of a wavelength of the ultrasonic wave. If the acoustic matching layer 3 as described above is continuously arranged in a transverse direction along the direction in which the transducer elements 1, 1, ... are arranged, a crosstalk between the channels (an radio interference between signals) is increased due to the ultrasonic wave propagating through the acoustic matching layer 3. Accordingly, incisions are made into the acoustic matching layer 3 in correspondence with gaps 6, 6, ... between the channels of the plurality of transducer elements 1, 1, ... arranged with a predetermined pitch, thereby forming gaps 7, 7, ... between the channels to reduce the crosstalk.

However, in such a conventional ultrasonic probe, since the above-mentioned acoustic matching layer 3 is formed using a uniform material having an acoustic impedance of an intermediate value between the acoustic impedance of the transducer element 1 and that of the object to be examined, the acoustic matching layer 3 does not perform a pure piston movement in only a direction in which an ultrasonic wave is transmitted from the transducer element 1, but oscillates also in a direction perpendicular to the transmitted direction of the ultrasonic wave. The existence of such an oscillation mode in the direction perpendicular to the transmitted direction of the ultrasonic wave in each acoustic matching layer 3 is harmful to an original purpose of the ultrasonic wave transmission/reception. The reason is that, if an ultrasonic wave is transmitted at a frequency close to the oscillation frequency in the transverse direction, a part of the energy thereof is used for the oscillation of the acoustic matching layer in the transverse direction, so that an original response in the longitudinal direction is deteriorated.

Figure 12:
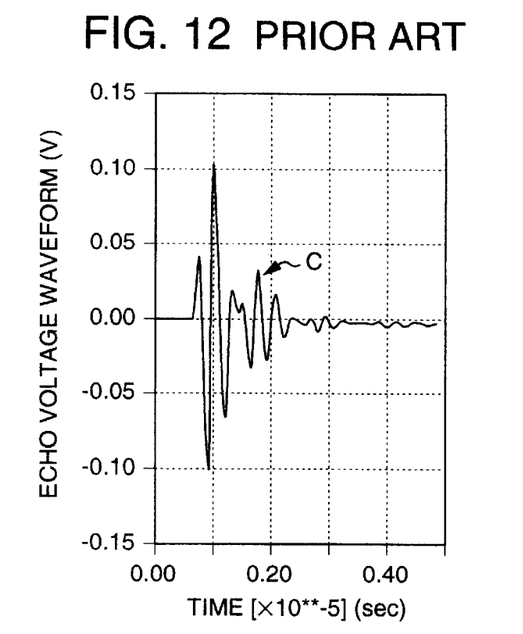
FIG. 12 is a graph for showing a state in which Round Trip Impulse Response is simulated in the conventional ultrasonic probe.
Figure 13:
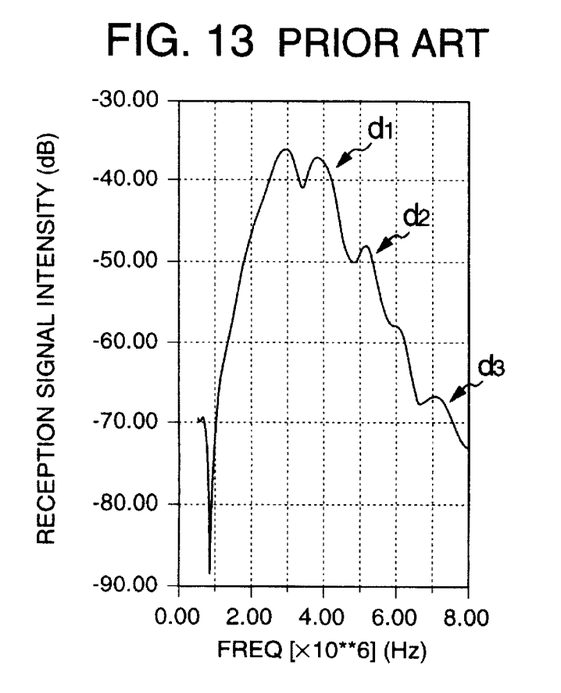
FIG. 13 is a graph for showing a state in which Round Trip Frequency Response is simulated in the conventional ultrasonic probe.

For example, as is seen in a simulation on Round Trip Impulse Response shown in FIG. 12, there occurred an irregular tail-trailing c in the echo voltage waveform with a lapse of time, so that a pulse characteristic of a reception signal becomes worse. Also, as is seen in a simulation on Round Trip Frequency Response shown in FIG. 13, there occurred ripples $d_1$, $d_2$, and $d_3$ at certain frequencies, so that a broad frequency characteristic is not obtained. On account of this, in the conventional ultrasonic probe, it is not able to optimize the oscillation mode in the direction perpendicular to the transmitted direction of the ultrasonic wave in the acoustic matching layer 3. This eventually brought about no broad frequency characteristic or no excellent pulse response characteristic, thus, in some cases, resulting in a deterioration in image quality of an ultrasonic wave image.

SUMMARY OF THE INVENTION

Accordingly, it is an object of the present invention to provide, in order to deal with the above-described problems, an ultrasonic probe capable of reducing a crosstalk between the channels and having a broad frequency characteristic and an excellent pulse response characteristic, and an ultrasonic diagnostic apparatus using the ultrasonic probe.

In order to attain the above-described object, the ultrasonic probe according to the present invention includes a plurality of transducer elements which are arranged with a predetermined pitch so as to form each of channels and transmits an ultrasonic wave and receives a reflected wave from inside of an object to be examined, electrodes provided on a front surface and a rear surface of each of the transducer elements so as to apply a voltage thereto, and an acoustic matching layer for taking a matching of an acoustic impedance between the above-described transducer elements and the object to be examined, wherein the above-described acoustic matching layer is constituted so that the acoustic matching layer has an anisotropy in an acoustic characteristic between a direction in which the ultrasonic wave is transmitted from the transducer elements above-mentioned and a direction perpendicular to the transmitted direction of the ultrasonic wave.

The phrase "the acoustic matching layer has anisotropies" means that, in the acoustic matching layer, a speed of an ultrasonic wave differs depending on whether it propagates in the longitudinal direction or in the transverse direction, and an attenuation rate of intensity of an ultrasonic wave differs depending on whether it propagates in the longitudinal direction or in the transverse direction.

Also, the ultrasonic diagnostic apparatus as a related invention includes an ultrasonic probe for transmitting or receiving an ultrasonic wave into or from the object to be examined, an ultrasonic beam forming unit which drives the ultrasonic probe and transmits the ultrasonic wave and processes a reflected echo signal received by the ultrasonic probe and forms an ultrasonic beam, an image processing device for constructing an ultrasonic wave image with the input of the received signal from the ultrasonic beam forming unit and a display device for displaying an image by taking in the image signal from the image processing device, wherein an ultrasonic probe having an acoustic matching layer which has an anisotropy in the acoustic characteristic between an ultrasonic wave-transmitting direction from the transducer elements and a direction perpendicular thereto, is employed as the above-described ultrasonic probe.

Since the present invention is constituted as described above, it is possible to reduce the crosstalk between the channels and obtain the broad frequency characteristic and the excellent pulse response characteristic. This makes it possible to enhance image quality of an ultrasonic wave image.

Further, as to the ultrasonic diagnostic apparatus as the related invention, since the ultrasonic probe according to the present invention which is structured as stated above is used as an ultrasonic probe, the crosstalk between the respective channels can be reduced and an ultrasonic diagnostic apparatus having a broad frequency characteristic and an excellent pulse response characteristic can be realized.

DESCRIPTION OF THE PREFERRED EMBODIMENTS

Based on the accompanying drawings, the description will be given below in detail concerning an embodiment of the present invention.

Figure 1:
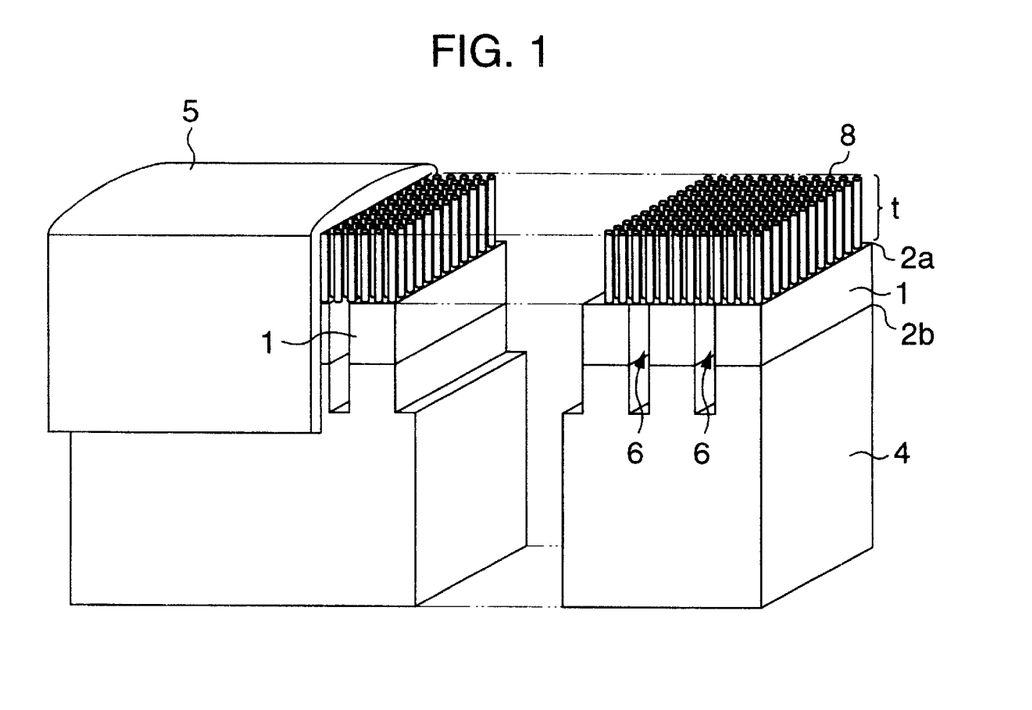
FIG. 1 is a partial cross sectional perspective view for showing a first embodiment of an ultrasonic probe according to the present invention.

FIG. 1 is a partial cross sectional perspective view for showing a first embodiment of an ultrasonic probe according to the present invention. The ultrasonic probe transmits an ultrasonic wave to an object to be examined and receives a reflected wave of the transmitted ultrasonic wave. As shown in FIG. 1, the ultrasonic probe includes a plurality of transducer elements 1, 1, . . . , electrodes 2a, 2b, and an acoustic matching layer 8.

The above-described transducer elements 1 are embers which transmit the ultrasonic wave to the object to be examined and receive the reflected wave from a diagnosis part. The transducer elements 1 are arranged with a predetermined pitch with a fixed length of gaps 6, 6, . . . , thus each of channels for transmitting and receiving the ultrasonic wave is formed. The electrodes 2a, 2b are provided on a front surface and a rear surface of each of the transducer elements, respectively. The electrodes 2a, 2b apply a voltage to the transducer element 1 so as to oscillate the transducer member and generate the ultrasonic wave. In addition to this, the electrodes 2a, 2b extract a voltage excited in the transducer element 1 which received the reflected wave. The electrodes 2a, 2b are connected to an ultrasonic wave transmitting-receiving circuit outside the drawing.

Also, the acoustic matching layer 8 is provided at a front side of the above-described transducer elements 1. The acoustic matching layer 8 takes a matching of an acoustic impedance between the transducer elements 1 and the object to be examined. An acoustic impedance of the acoustic matching layer 8 is, as a whole, set to be an intermediate value between an acoustic impedance of the transducer elements 1 and that of the object to be examined. Moreover, the acoustic matching layer 8 is formed so that a thickness (t) thereof becomes equal to ¼th of a wavelength of the ultrasonic wave.

In FIG. 1, a reference numeral 4 denotes a backing material for preventing an ultrasonic wave transmitted from a rear surface of the above-described transducer element 1 from getting back again to the rear surface thereof. A reference numeral 5 denotes an acoustic lens provided over the above-described acoustic matching layer 8 so as to focus an ultrasonic beam transmitted from the front surface of the transducer element 1. A material which is effective in attenuating an ultrasonic wave is employed as the above-described backing material 4.

In the present invention, the above-described acoustic matching layer 8 is constituted so that it has an anisotropy in the acoustic characteristics between a direction in which an ultrasonic wave is transmitted from the above-described transducer element 1 and a direction perpendicular to the ultrasonic wave-transmitting direction. More preferably, the acoustic matching layer 8 is constituted so that an ultrasonic wave is attenuated more greatly in the direction perpendicular to the ultrasonic wave-transmitting direction than in the ultrasonic wave-transmitting direction. On account of this, the acoustic matching layer 8 is composed of a composite material formed by combining a plurality of kinds of materials each of which has a different acoustic impedance.

Figure 2:
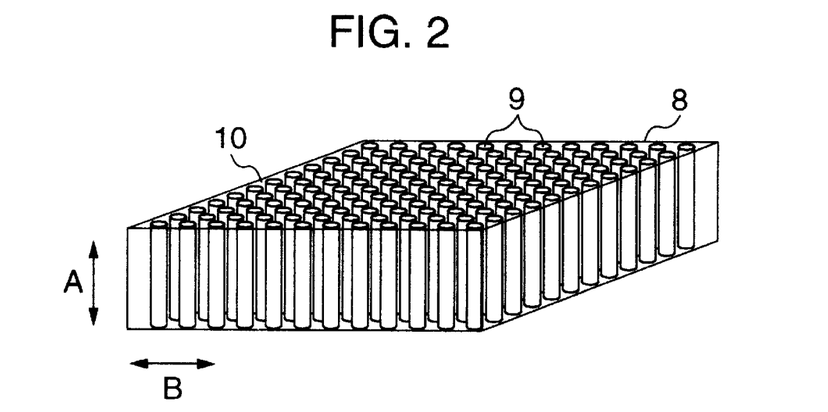
FIG. 2 is a perspective view for illustrating an example of structure of an acoustic matching layer in the above-described ultrasonic probe.

For example, as shown in FIG. 2, among a plurality of kinds of materials, a material 9 having a higher acoustic impedance is formed in a pole-like configuration, and a large number of pole-like materials 9 having a higher acoustic impedance are arranged. Then, spaces among them are filled with a material 10 having a lower acoustic impedance, thereby forming the acoustic matching layer 8 having a plate-like configuration with a predetermined thickness as a whole. The substances employable as the materials 9 having a higher acoustic impedance are metals such as aluminum or magnesium, or ceramics, glass, and so on. Also, the substances available as the material 10 having a lower acoustic impedance are nylon, polyurethane, an epoxy resin, a plastic material, and so on. In the example in FIG. 2, the material 9 having a higher acoustic impedance is formed in advance in the pole-like configuration with a predetermined length by machining or molding, and a large number of them are arranged. Then, the material 10 having a lower acoustic impedance, for example, a plastic material, is poured into spaces among them. Finally, a thickness of the whole structure is processed, thus fabricating the acoustic matching layer 8 formed in the plate-like configuration with a predetermined thickness and having the anisotropy in the acoustic characteristic.

Also, as another embodiment, the impedance of the material 10 having a lower acoustic impedance may be further lowered by mixing materials such as balloons containing a gas or beads with a substance such as an epoxy resin. Also, as a still another embodiment, the portion of the material 10 may be filled with a gas or a liquid, or the portion of the material 10 may be evacuated.

The acoustic matching layer 8 constituted as described above has an anisotropy. Namely, in FIG. 2, in a longitudinal direction (A direction) of the materials 9 having a higher acoustic impedance, the ultrasonic wave propagates at a speed which is substantially equal to a speed of a sound propagating in the materials 9 having the higher acoustic impedance, and, in a transverse direction (B direction) perpendicular to the above-mentioned longitudinal direction, the ultrasonic wave propagates at a comparatively low speed which is substantially equal to a speed of a sound propagating in the material 10 having the low acoustic impedance.

Since the ultrasonic probe according to the present invention is constituted as described above, it is possible to suppress the occurrence of the unnecessary oscillation mode in the direction perpendicular to the ultrasonic wave-transmitting direction in the acoustic matching layer 8 of each channel. Accordingly, the cross-talk between the respective channels can be reduced and a broad frequency characteristic and an excellent pulse response characteristic can be obtained.

Figure 8:
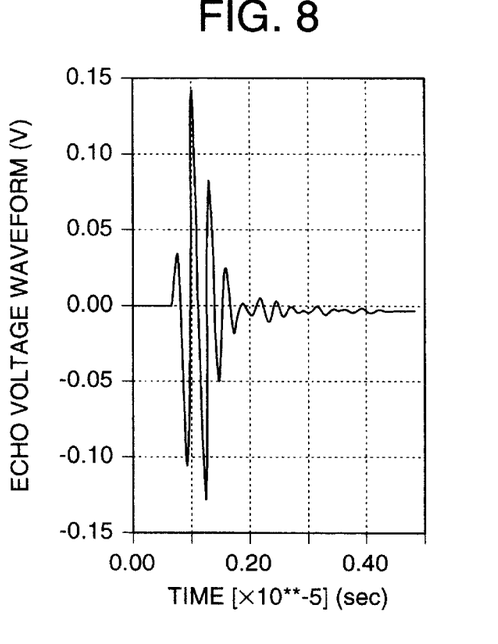
FIG. 8 is a graph for showing a state in which Round Trip Impulse Response is simulated in the ultrasonic probe according to the present invention.
Figure 9:
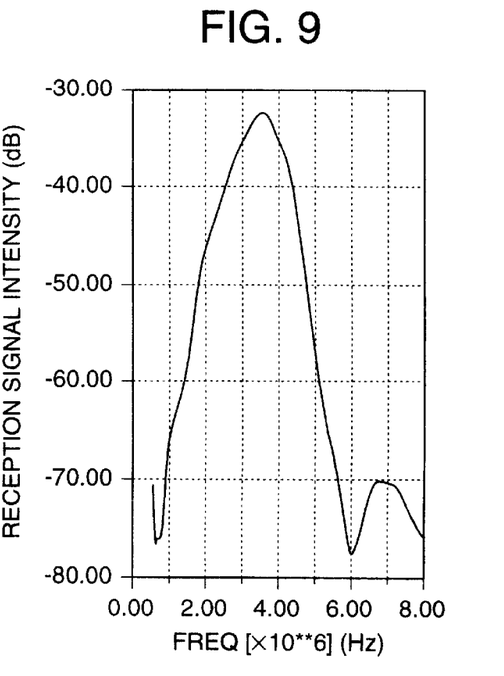
FIG. 9 is a graph for showing a state in which Round Trip Frequency Response is simulated in the ultrasonic probe according to the present invention.

For example, as is seen in a simulation on Round Trip Impulse Response shown in FIG. 8, there occurs no irregular tail-trailing as indicated by "c" in FIG. 12 in the echo voltage waveform with a lapse of time. This improves the pulse characteristic of a reception signal. Also, as is seen in a simulation on Round Trip Frequency Response shown in FIG. 9, unlike the prior art, there occurs no ripple at certain frequencies, and the frequency characteristic becomes broad and a sensitivity is also improved.

Furthermore, as shown in FIG. 1, the acoustic matching layer 8 having such anisotropy in the acoustic characteristic is installed in such a state that the longitudinal direction of the materials 9 having a higher acoustic impedance is made to coincide with the ultrasonic wave-transmitting direction from the above-described transducer elements 1, 1, . . . . By this, the ultrasonic wave can be more greatly attenuated in the direction perpendicular to the wave-transmitting direction than in the ultrasonic wave-transmitting direction. Consequently, without forming gaps 7, 7, . . . in the acoustic matching layer 3 in a conventional embodiment shown in FIG. 11, the crosstalk between the respective channels can be reduced.

Figure 3:
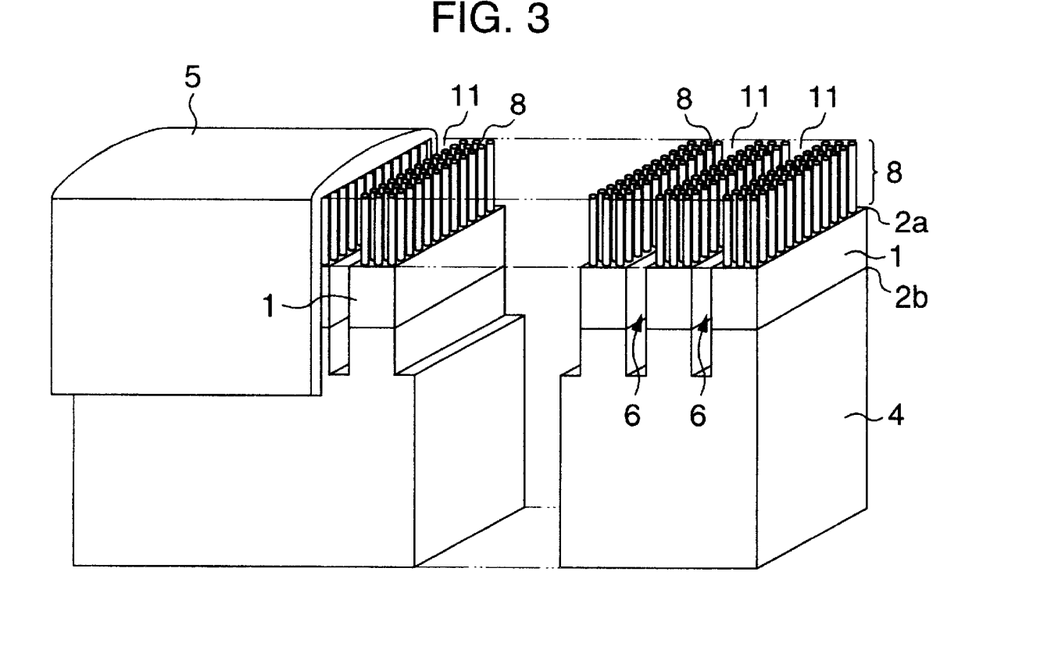
FIG. 3 is a partial cross sectional perspective view for illustrating a second embodiment of the ultrasonic probe according to the present invention.

FIG. 3 is a partial cross sectional perspective view for illustrating a second embodiment of the ultrasonic probe according to the present invention. In this embodiment, incisions are made into the above-described acoustic matching layer 8 in correspondence with the gaps 6, 6, . . . between the channels on a plurality of the transducer elements 1, 1, . . . arranged with the predetermined pitch, thereby forming gaps 11, 11, . . . between the respective channels. In this case, since the acoustic matching layer 8 is separated for each channel by a gap 11, an oscillation of the acoustic matching layer 8 is not transmitted in a transverse direction, so that the crosstalk between the respective channels can be more reduced as compared with the embodiment in FIG. 1.

Figure 4:
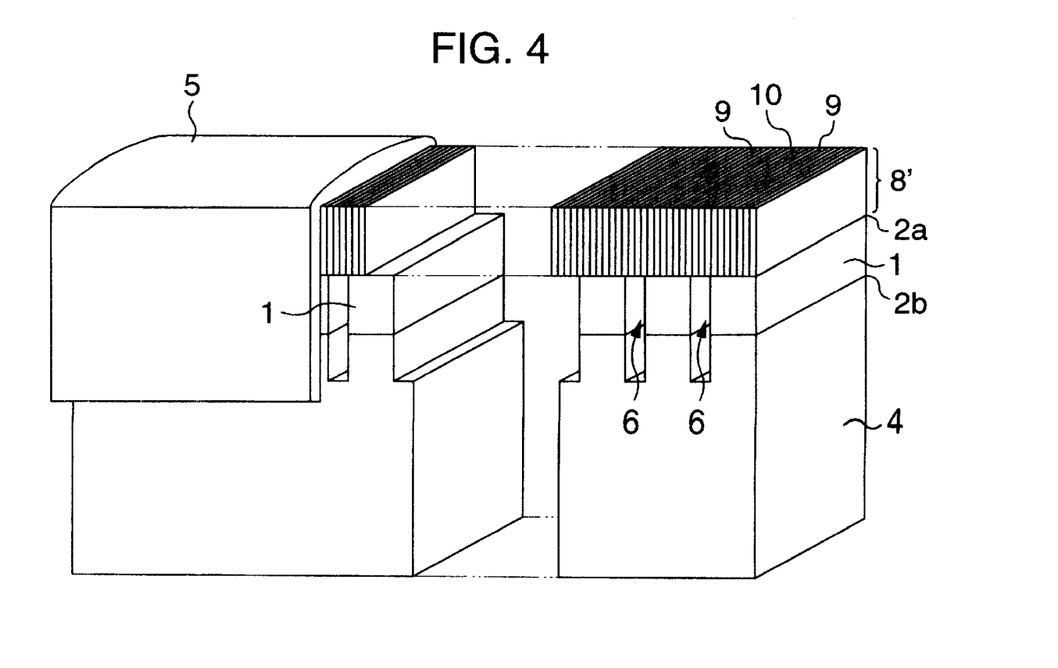
FIG. 4 is a partial cross sectional perspective view for illustrating a third embodiment of the ultrasonic probe according to the present invention.
Figure 5:
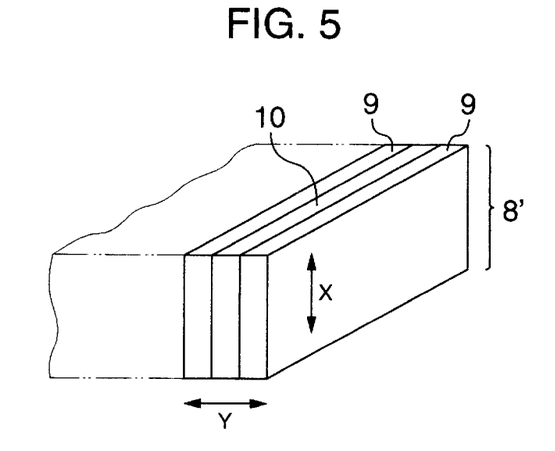
FIG. 5 is an essential part perspective view for illustrating an example of structure of an acoustic matching layer in the above-described third embodiment of the ultrasonic probe.

FIG. 4 is a partial cross sectional perspective view for illustrating a third embodiment of the ultrasonic probe according to the present invention. In this embodiment, an acoustic matching layer 8' is formed with a composite material of a material 9 having a strip and plate like shape and a higher acoustic impedance and a material 10 having a strip and plate like shape and a lower acoustic impedance. The materials 9 and 10 are arranged alternately in a sandwich-like structure in a transverse direction as shown in FIG. 5. The acoustic matching layer 8' is formed into a plate-like configuration with a predetermined thickness as a whole. The acoustic matching layer 8' formed as described above has an anisotropy in the acoustic characteristic between a thickness direction (X direction) of the plate-like configuration and a transverse direction (Y direction) perpendicular thereto. Namely, in the above-described thickness direction (X direction) of the plate-like configuration, an ultrasonic wave propagates at a speed which is close to a speed of a sound propagating in the materials 9 having a higher acoustic impedance, and, in the transverse direction (Y direction) perpendicular to the thickness direction, the ultrasonic wave propagates at a speed which is close to a speed of a sound propagating in the materials 10 having a low acoustic impedance.

In this way, the above-described acoustic matching layer 8' for each of the channels is composed of the composite material formed by combining the plurality of kinds of materials 9, 10, each has a different acoustic impedance. As a result, the acoustic matching layer 8' is constituted in such a state that it has the anisotropies in the acoustic characteristic between the ultrasonic wave-transmitting direction from the transducer elements 1, 1, . . . and the direction perpendicular thereto. Consequently, the occurrence of the unnecessary oscillation mode in the direction perpendicular to the ultrasonic wave-transmitting direction in the acoustic matching layer 8' for each of the channels can be suppressed. Accordingly, the crosstalk between the respective channels can be reduced and the broad frequency characteristic and the excellent pulse response characteristic can be obtained.

In this case, at least two layers of the material 10 having a low acoustic impedance are provided on an ultrasonic wave transmitting surface of each of the channels.

Furthermore, as shown in FIG. 4, the acoustic matching layer 8' having such anisotropy in the acoustic characteristic is installed in such a state that the above-described thickness direction (X direction) of the plate-like configuration is made to coincide with the ultrasonic wave-transmitting direction from the transducer elements 1, 1, . . . . By this, an ultrasonic wave can be more greatly attenuated in the direction perpendicular to the ultrasonic wave-transmitting direction than in the ultrasonic wave-transmitting direction. Consequently, without forming the aps 7, 7, . . . in the acoustic matching layer 3 in the conventional embodiment shown in FIG. 11, the crosstalk between the respective channels can be reduced.

Figure 6:
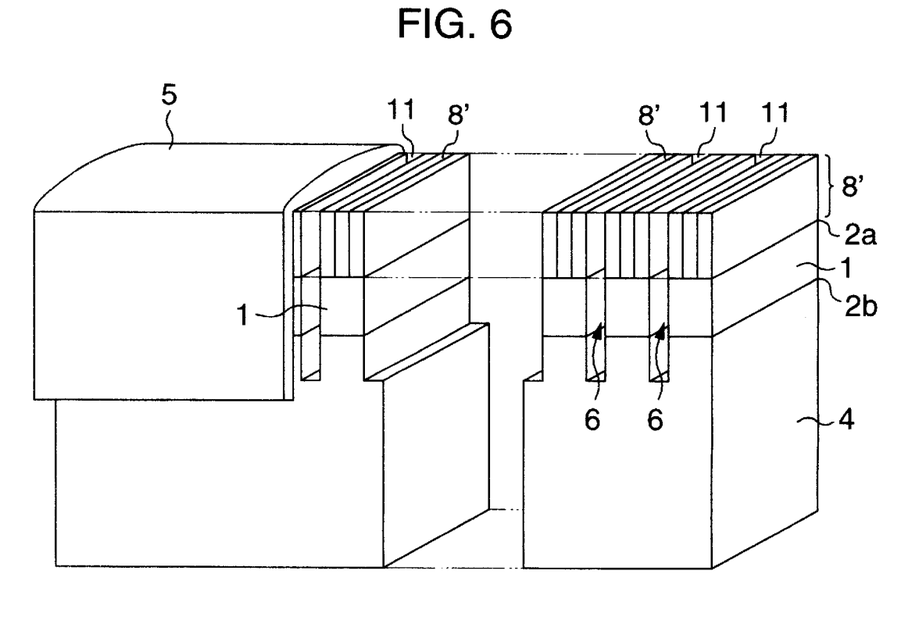
FIG. 6 is a partial cross sectional perspective view for illustrating a fourth embodiment of the ultrasonic probe according to the present invention.

FIG. 6 is a partial cross sectional perspective view for illustrating a fourth embodiment of the ultrasonic probe according to the present invention. In this embodiment, incisions are made into the above-described acoustic matching layer 8' in correspondence with gaps 6, 6, . . . between the respective channels of a plurality of the transducer elements 1, 1, . . . arranged with a predetermined pitch, thereby forming gaps 11, 11, . . . between the respective channels. In this embodiment, since the acoustic matching layer 8' is separated by a gap 11 at every channel, the oscillation of the acoustic matching layer 8' does not transmit in a transverse direction, so that the crosstalk between the respective channels can be more reduced as compared with the embodiment in FIG. 4.

Also, as another embodiment, the impedance of the material 10 having a lower acoustic impedance may be further lowered by mixing materials such as balloons containing a gas or beads with a substance such as an epoxy resin. Also, as a still another embodiment, the portion of the material 10 may be filled with a gas or a liquid, or the portion of the material 10 may be evacuated.

Figure 7:
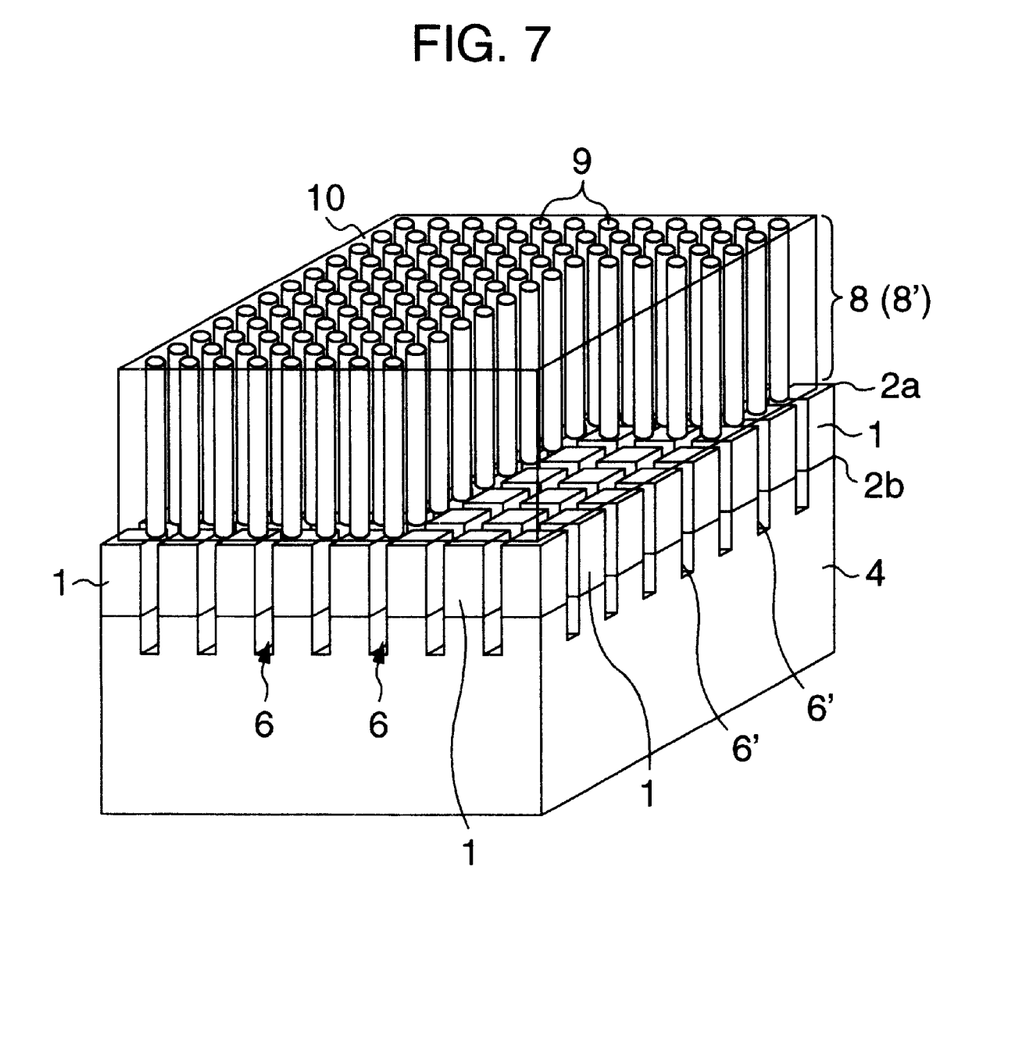
FIG. 7 is a partial-omission perspective view for illustrating a fifth embodiment of the ultrasonic probe according to the present invention.

FIG. 7 is a partial-omission perspective view for illustrating a fifth embodiment of the ultrasonic probe according to the present invention. In the embodiments described earlier, the plurality of transducer elements 1, 1, are arranged one-dimensionally with a predetermined pitch. In the present embodiment, however, a plurality of transducer elements 1, 1, . . . are arranged two-dimensionally with a formation of the gaps 6', 6', . . . with a predetermined pitch in a depth direction. And, the above-mentioned acoustic matching layer 8 or 8' is located on the side of a front surface of the transducer elements 1, 1, . . . arranged two-dimensionally. In this embodiment, in a two-dimensional array type ultrasonic probe, the crosstalk between the respective channels can be reduced and a broad frequency characteristic and an excellent pulse response characteristic can be obtained.

Figure 10:
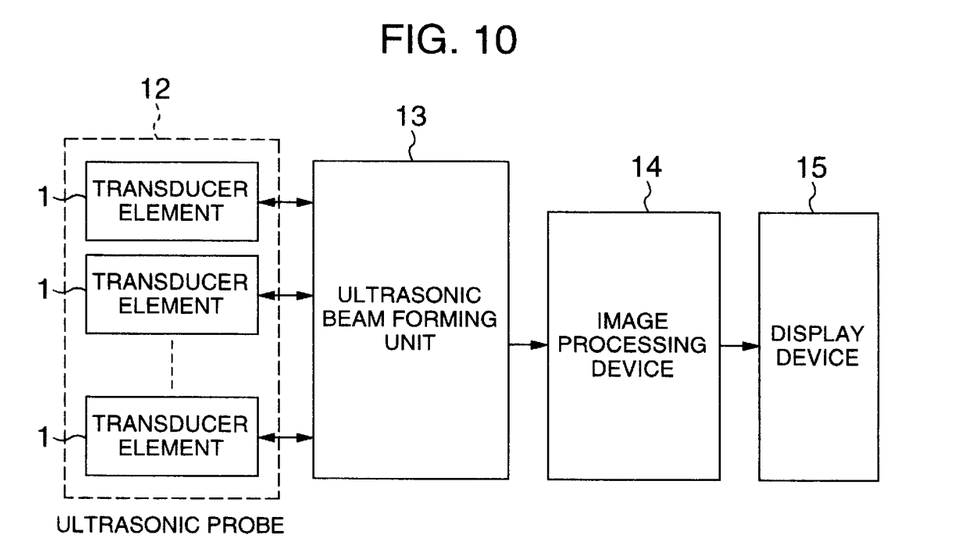
FIG. 10 is a block diagram showing a whole configuration of an ultrasonic diagnostic apparatus using the ultrasonic probe configured as above according to the present invention.

FIG. 10 is a block diagram showing a whole configuration of an ultrasonic diagnostic apparatus using the ultrasonic probe configured as mentioned above according to the present invention. Namely, as shown in FIG. 10, the ultrasonic diagnostic apparatus includes an ultrasonic probe 12 for transmitting and receiving an ultrasonic wave into or from an object to be examined, an ultrasonic beam forming unit 13 which drives the ultrasonic probe 12 so as to cause it to generate the ultrasonic wave and processes a reflected echo signal received by the ultrasonic probe 12 so as to form an ultrasonic beam, an image processing device 14 for constructing an ultrasonic image with an input of the received signal from the ultrasonic beam forming unit 13, and a display device 15 for displaying an image by taking in the image signal from the image processing device 14, wherein an ultrasonic probe described in any one of FIGS. 1, 3, 4, 6 or 7 is employed as the above-described ultrasonic probe 12. In this case, an ultrasonic diagnosis apparatus can be realized in which the crosstalk between the channels in the ultrasonic probe 12 can be reduced and a broad frequency characteristic and an excellent pulse response characteristic can be obtained.

The present invention is not limited to the embodiments disclosed above, but rather includes various modifications involved within the spirit of the claims.

We claim:

1. An ultrasonic probe, comprising a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer has an anisotropy in acoustic characteristic between an ultrasonic wave-transmitting direction from said transducer elements and a direction perpendicular to the ultrasonic wave-transmitting direction;

wherein said acoustic matching layer includes a plurality of regions each of which has a different acoustic impedance on an acoustic transmission surface of each transducer element constituting one channel;

wherein said plurality of regions each of which has a different acoustic impedance are arranged in said direction perpendicular to said ultrasonic wave-transmitting direction;

wherein said plurality of regions include a first region and at least two second regions, said first region having a predetermined acoustic impedance on said acoustic transmission surface of each transducer element constituting one channel, said second regions being separately arranged by said first region and having an acoustic impedance which is higher than the predetermined acoustic impedance of said first region; and wherein said first region and said second regions include a long and thin plate-like region, respectively, and said second regions are arranged via said first region.

2. An ultrasonic probe, comprising:

a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer has an anisotropy in acoustic characteristic between an ultrasonic wave-transmitting direction from said transducer elements and a direction perpendicular to the ultrasonic wave-transmitting direction;

wherein said acoustic matching layer includes a plurality of regions each of which has a different acoustic impedance on an acoustic transmission surface of each transducer element constituting one channel;

wherein said plurality of regions each of which has a different acoustic impedance are arranged in said direction perpendicular to said ultrasonic wave-transmitting direction;

wherein said plurality of regions include a first region and at least two second regions, said first region having a predetermined acoustic impedance on said acoustic transmission surface of each transducer element constituting one channel, said second regions being separately arranged by said first region and having an acoustic impedance which is higher than the predetermined acoustic impedance of said first region; and wherein said acoustic matching layer includes one of, liquid and a vacuum region in said first region.

3. An ultrasonic probe according to claim 6, wherein said acoustic matching layer is formed in such a manner that it is spatially separated for each channel.

4. An ultrasonic probe, comprising:

a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer includes a plurality of regions each of which has a different acoustic impedance on an acoustic transmission surface of each transducer element constituting one channel, and a manner in which said plurality of regions are arranged differs between an ultrasonic wave-transmitting direction from said transducer elements and a direction perpendicular to the ultrasonic wave-transmitting direction;

wherein said plurality of regions are arranged in said direction perpendicular to said ultrasonic wave-transmitting direction with a predetermined space formed therebetween;

wherein said plurality of regions include a first region having a first acoustic impedance and a second region having a second acoustic impedance which is higher than said first acoustic impedance, and said first region and said second region are arranged alternately on said acoustic transmission surface of the transducer element constituting one channel, and there exist at least two said second regions; and wherein said first region and said second regions are formed in a long and thin plate-like configuration.

5. An ultrasonic probe, comprising:

a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer includes a plurality of regions each of which has a different acoustic impedance on an acoustic transmission surface of each transducer element constituting one channel, and a manner in which said plurality of regions are arranged differs between an ultrasonic wave-transmitting direction from said transducer elements and a direction perpendicular to the ultrasonic wave-transmitting direction;

wherein said plurality of regions are arranged in said direction perpendicular to said ultrasonic wave-transmitting direction with a predetermined space formed therebetween;

wherein said plurality of regions include a first region having a first acoustic impedance and a second region having a second acoustic impedance which is higher than said first acoustic impedance, and said first region and said second region are arranged alternately on said acoustic transmission surface of the transducer element constituting one channel, and there exist at least two said second regions; and wherein said acoustic matching layer includes one of, liquid and a vacuum region in said first region.

6. An ultrasonic probe according to claim 4, wherein said acoustic matching layer is formed in such a manner that it is spatially separated for each channel.

7. An ultrasonic diagnostic apparatus, comprising:

an ultrasonic probe as claimed in any one of claims 1, 2, 3, 4 and 6 for transmitting and receiving an ultrasonic wave into and from an object to be examined;

an ultrasonic beam forming unit for driving said ultrasonic probe to transmit an ultrasonic wave and processing a reflected echo signal received by said ultrasonic probe and forming an ultrasonic beam;

an image processing unit for constructing an ultrasonic image with input of a reception signal from said ultrasonic beam forming unit; and a display unit for displaying an image by taking in an image signal from said image processing unit.

8. An ultrasonic probe according to claim 1, wherein said long and thin plate-like region includes plate-like members having an axis thereof extending in the ultrasonic wave-transmitting direction.

9. An ultrasonic probe according to claim 4, wherein said long and thin plate-like region includes plate-like members having an axis thereof extending in the ultrasonic wave-transmitting direction.

10. An ultrasonic probe, comprising:

a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer includes a first region of polymer material having a predetermined acoustic impedance and a second region of non-polymer material having an acoustic impedance larger than that of said first region, and said first and second regions are located on an acoustic transmission surface of a transducer element forming one channel and arranged in a perpendicular direction to an ultrasonic wave-transmitting direction, and said acoustic matching layer has an anisotropy in acoustic characteristic between said ultrasonic wave-transmitting direction and a direction perpendicular to said ultrasonic wave-transmitting direction;

wherein said first and second regions are arranged in an alternate manner, and each of said first and second regions is formed in a thin and long plate shape having a dimension in said ultrasonic wave-transmitting direction which is shorter than a dimension in a direction which is perpendicular to both a direction of the arrangement of said first a nd second regions and said ultrasonic wave-transmitting direction.

11. An ultrasonic probe according to claim 10, wherein said acoustic matching layer is continuously arranged over a plurality of channels in said direction perpendicular to said ultrasonic wave-transmitting direction.

12. An ultrasonic probe according to claim 10, wherein said acoustic matching layer is separated for each channel.

13. An ultrasonic probe, comprising:

a plurality of transducer elements which are arranged with a predetermined pitch so as to form each channel for transmitting an ultrasonic wave and receiving a reflected ultrasonic wave from inside of an object to be examined;

electrodes for applying a voltage to said transducer elements; and an acoustic matching layer for taking a matching of an acoustic impedance between said transducer elements and the object to be examined, wherein said acoustic matching layer includes a first region of polymer material having a predetermined acoustic impedance and a second region of non-polymer material having an acoustic impedance larger than that of said first region, and said first and second regions are located on an acoustic transmission surface of a transducer element forming one channel and arranged in a perpendicular direction to an ultrasonic wave-transmitting direction, and a manner of arrangement of said first and second regions is different between said ultrasonic wave-transmitting direction and a direction perpendicular to said ultrasonic wave-transmitting direction;

wherein said first and second regions are arranged in an alternate manner, and each of said first and second regions is formed in a thin and long plate shape having a dimension in said ultrasonic wave-transmitting direction which is shorter than a dimension in a direction which is perpendicular to both a direction of the arrangement of said first and second regions and said ultrasonic wave-transmitting direction.

14. An ultrasonic probe according to claim 13, wherein said acoustic matching layer is continuously arranged over a plurality of channels in said direction perpendicular to said ultrasonic wave-transmitting direction.

15. An ultrasonic probe according to claim 13, wherein said acoustic matching layer is separated for each channel.

16. An ultrasonic diagnostic apparatus, comprising:

an ultrasonic probe as claimed in any one of claims 10, 11, 12, 13, 14 and 15 for transmitting and receiving an ultrasonic wave into and from an object to be examined;

an ultrasonic beam forming unit for driving said ultrasonic probe to transmit an ultrasonic wave and processing a reflected echo signal received by said ultrasonic probe and forming an ultrasonic beam;

an image processing unit for constructing an ultrasonic image with input of a reception signal from said ultrasonic beam forming unit; and a display unit for displaying an image by taking in an image signal from said image processing unit.

\* \* \* \* \*